United States Patent [19]

Bradford et al.

[11] Patent Number: Plant 5,664

[45] Date of Patent: Feb. 18, 1986

[54] NECTARINE TREE (SEPTEMBER RED)

[76] Inventors: Norman G. Bradford; Lowell G. Bradford, both of 11875 E. Savana Rd., Le Grand, Calif. 95333

[21] Appl. No.: 622,089

[22] Filed: Jun. 18, 1984

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

The present invention relates to a clingstone nectarine tree and more particularly to a new and distinct variety broadly characterized by a medium size, vigorous, hardy, very productive and regular bearing tree, the fruit of which ripens around five days later than September Grand (U.S. Plant Pat. No. 1,755) variety under the ecological conditions described. The skin of the fruit has a more exceptional red blush skin coloring at picking time compared to other late varieties which are known to us, is of outstanding firmness for shipping, and will remain picking ripe on the tree for about two weeks. The fruit is of excellent taste and has attractive form, and we believe it to be the best late shipping nectarine available.

1 Drawing Figure

BACKGROUND OF THE VARIETY

The instant variety of nectarine tree was produced by us at Bradford Farms in Merced County (San Joaquin Valley), Calif., as the result of the pollination of the seed parent, which is a cross of Red Free nectarine (U.S. Plant Pat. No. 3,385) and Tom Grand nectarine (U.S. Plant Pat. No. 2,895), by Sparkling Red nectarine (U.S. Plant Pat. No. 4,314). Subsequent to origination of the instant variety of nectarine tree, we asexually reproduced it by budding and grafting, and such reproduction of plant and fruit characteristics were true to the original plant in all respects.

Although the instant variety is ready for first picking about five days later than September Grand, it is distinguished from and an improvement on that variety as well as other varieties of late maturing nectarines known to us by having a redder skin color at picking time, being firmer, and having an exceptionally long storage time on the tree of at least two weeks, under the ecological conditions described, and having a better flavor than the varieties cited herein.

The instant variety is distinguished from, and an improvement on Tom Grand nectarine, by ripening about 16 days later, having more red skin color, and being much firmer. It is distinguished from Red Free in being a clingstone instead of a freestone, and an improvement thereon by ripening about 46 days later. It differs from Sparkling Red in being a clingstone instead of a freestone, and an improvement thereon by ripening about 35 days later. It is further distinguished from and an improvement on other late ripening varieties of nectarines known to us by having a redder skin color at picking time, by ripening later and having an a more exceptional long storage time on the tree of about two weeks, and a longer shelf life, under the ecological conditions described. It also has a better flavor than other late varieties known to us.

DRAWINGS

The accompanying photograph includes views of whole fruits, showing the characteristics of form and skin color, a fruit divided on its suture plane showing flesh color and stone cavity, and a characteristic stone. Although the fruit is of a uniform, medium size, having a diameter averaging $2\frac{1}{2}''$ in both the axial diameter and traverse the suture plane, the angle at which the fruit was photographed shows a perspective great enough to give the appearance of variable size fruit.

POMOLOGICAL CHARACTERISTICS

Referring now more specifically to the pomological characteristics of this new and distince variety of nectarine tree, the following has been observed by me under the ecological conditions prevailing near Le Grand, Merced County (San Joaquin Valley), Calif., and was developed at the state of eating ripeness in the 1983 growing season. All color plate identifications are by reference to *Dictionary of Color* 1950 (2nd ed.) by Maerz and Paul.

TREE

General: Medium size, vigorous, regular bearing and very productive; dense, vase formed, and spreading.

Trunk: Of medium size, shaggy; color resembling Raquet (15 C-7), with numerous tan lenticles ranging from small to large in size.

Branches: Medium size, medium smooth; resembling Brown Doraul (14 A-12) on dorsal side and Alamo (greenish brown) on ventral side; numerous small tan (14 F-11) lenticles.

LEAVES

Size: Length, $5\frac{1}{4}''$, width, $1\frac{1}{4}''$—large in size. Medium thickness.

Form: Elliptical.

Base: Acute.

Apex: Acuminate.

Surface: Smooth.

Color: Green (22 A-8) on dorsal side, Green (22 J-3) on ventral.

Margin: Crenate.

Venation: Pinnately net veined.

Petiole: Medium length, average $\frac{3}{8}''$; medium thickness.

Glands: Averaging two to four oppositely disposed on petiole and base of blade; medium size, reniform, green.

Stipules: A few, averaging $\frac{1}{8}''$ to $1/16''$

Leaf buds: Pointed.

FLOWERS

Buds: Hardy, large size, medium length, plump, free and pubescent.

Flowers: Late blooming date compared with other varieties; large size, pink. Some double blossoms were observed in the 1983 growing season.

FRUIT

Maturity when described: Eating ripe, on Sept. 19, 1983.

Size: Uniformly medium size; averaging 2½" axial diameter, 2½" transverse in suture plane.

Form: Unform, symmetrical; globose in both the longitudinal section and transverse through the diameter.

Suture: A deep suture which fills out somewhat with maturity extending from base to beyond apex; has marked depression at pistil point.

Ventral and dorsal surfaces: Rounded; lipped toward apex on both sides with unequal lips.

Cavity: Rounded; suture showing on both sides. Depth, ½", breadth, ⅜". Stem markings showing on most fruits. Base, truncate; apex, short, depressed.

Pistil point: Oblique, but negligible in size.

Stem: Medium size, ⅜" in length, 3/16" in width.

Skin:

*General.*—Medium thickness, medium texture; tenacious to flesh. Only slight tendency to crack.

*Color.*—Rose Beige (5 L-10) blush over yellow Ta Ming (10-L-6) under color. Takes on color early compared to other known late varieties. Exceptional red blush color at picking time.

Flesh:

*Color.*—Resembling Brass(11 L-6), with red next to the stone throught.

Amygdalin: Wanting.

Juice: Abundant.

Texture: Firm, crisp.

Fibres: Abundant, fine, tender.

Ripens: Evenly.

Flavor: Subacid.

Aroma: Very Slight.

Eating quality: Best.

STONE

Type: Clingstone.

Form: Obvoid.

Base: Straight.

Apex: Acute; equal sides.

Surface: Heavily ridged and grooved with pitting toward base.

Ridges: Jagged.

Color: Resembling Coffee (15 A-11).

Pit wall: ¼" thick.

Tendency to split: Only slight.

Kernel: Oval form, butter taste, viable. 9/16" in width.

Pellicle: Brown color.

Amygdalin: Abundant.

USE

For market, long distance shipping. Good to excellent keeping and shipping quality. The fruit has a long storage life on the tree after picking commences which provides an extended picking period.

I claim:

1. A new and distinct variety of clingstone nectarine tree, substantially as illustrated and described, which most nearly resembles the September Grand (U.S. Plant. Pat. No. 1,755) variety but is distinguished from and an improvement on that variety and other known late maturing varieties in having fruit which ripens about five days later than September Grand, has a more exceptional red skin color, and is firmer and remains picking ripe on the tree for approximately two weeks.

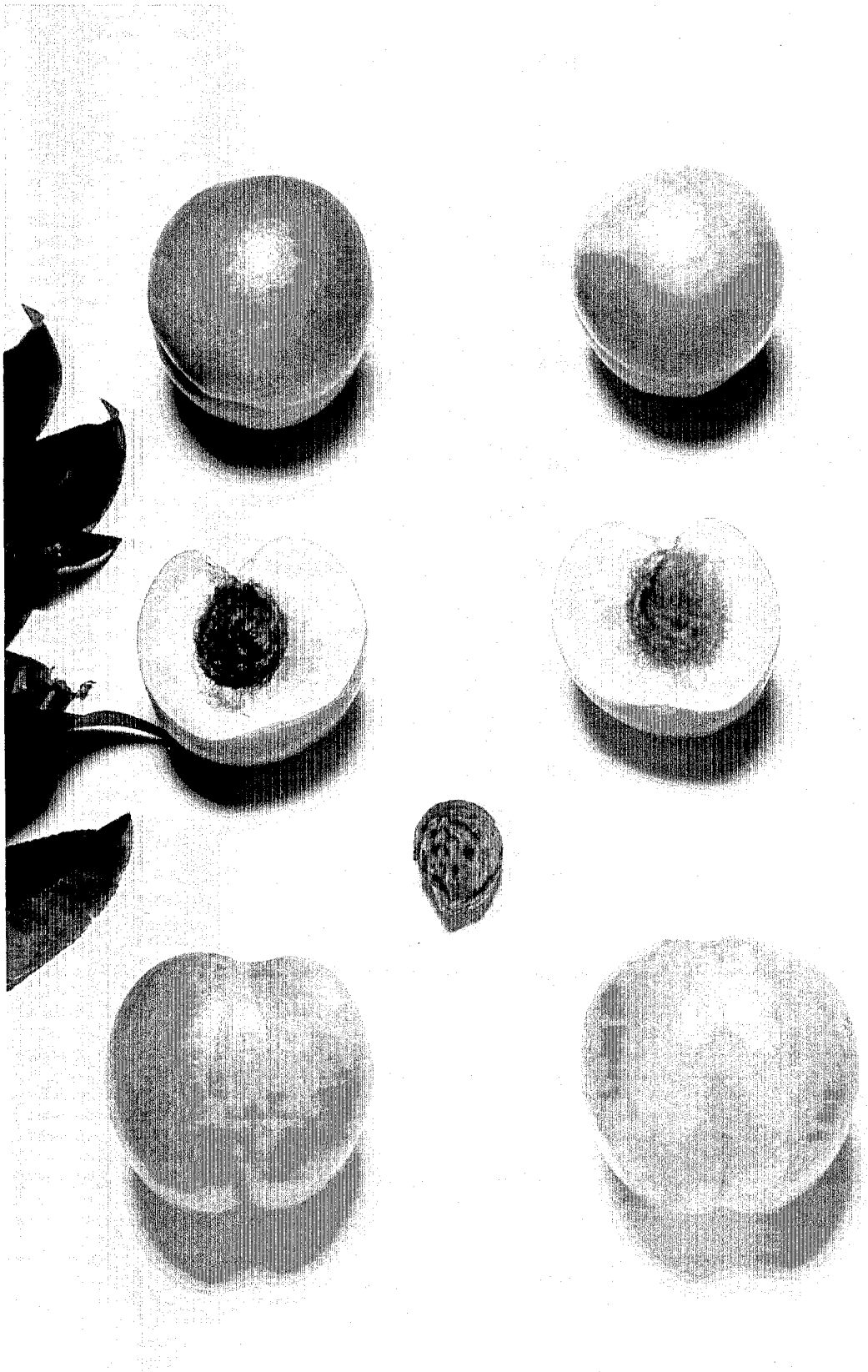

* * * * *